United States Patent [19]
Turpen

[11] Patent Number: 5,889,191
[45] Date of Patent: Mar. 30, 1999

[54] VIRAL AMPLIFICATION OF RECOMBINANT MESSENGER RNA IN TRANSGENIC PLANTS

[75] Inventor: Thomas H. Turpen, Vacaville, Calif.

[73] Assignee: Biosource Technologies, Inc., Vacaville, Calif.

[21] Appl. No.: 488,422

[22] Filed: Jun. 7, 1995

Related U.S. Application Data

[60] Division of Ser. No. 176,414, Dec. 29, 1993, which is a continuation-in-part of Ser. No. 997,733, Dec. 30, 1992, abandoned.

[51] Int. Cl.$^6$ .............................. A01H 5/00; C12N 15/40; C12N 15/83; C12N 15/82
[52] U.S. Cl. ..................... 800/288; 800/298; 435/69.1; 435/70.1; 435/235.1; 435/419; 435/468; 435/472; 435/475; 536/23.72
[58] Field of Search ................................. 435/69.1, 70.1, 435/172.3, 235.1, 240.4, 320.1, 419, 468, 472, 475; 536/23.72; 800/205, 288, 298

[56] References Cited

FOREIGN PATENT DOCUMENTS

| | | |
|---|---|---|
| B 7 195 191 | 3/1992 | Australia . |
| A 0 067 553 | 12/1982 | European Pat. Off. . |
| A 0 425 004 | 5/1991 | European Pat. Off. . |
| A 0 479 180 | 4/1992 | European Pat. Off. . |
| A 0 573 767 | 12/1993 | European Pat. Off. . |
| 63-14693 | 1/1988 | Japan . |
| WO A 8908145 | 9/1989 | WIPO . |
| WO 9012107 | 9/1990 | WIPO . |
| WO 9113994 | 9/1991 | WIPO . |

*Primary Examiner*—David T. Fox
*Attorney, Agent, or Firm*—Albert P. Halluin; John A. Bendrick; Howrey & Simon

[57] ABSTRACT

A novel method of over expressing genes in plants is provided. This method is based on the RNA amplification properties of plus strand RNA viruses of plants. A chimeric multicistronic gene is constructed containing a plant promoter, viral replication origins, a viral movement protein gene, and one or more foreign genes under control of viral subgenomic promoters. Plants containing one or more of these recombinant RNA transcripts are inoculated with helper virus. In the presence of helper virus recombinant transcripts are replicated producing high levels of foreign gene RNA.

Sequences are provided for the high level expression of the enzyme chloramphenicol acetyltransferase in tobacco plants by replicon RNA amplification with helper viruses and movement protein genes derived from the tobamovirus group.

14 Claims, 7 Drawing Sheets

TRANSGENE (cDNA)

TRANSCRIPTION

TRANSCRIPT (RNA)

RNA PROCESSING AND RNA REPLICATION

REPLICON (RNA)

P = PROMOTER
5'RO = 5' REPLICATION ORIGIN
FG = SEQUENCE CODING FOR FOREIGN GENE AS WELL AS OTHER SEQUENCES. DOES NOT CODE FOR COMPLETE SET OF VIRAL REPLICATION PROTEINS REQUIRED FOR REPLICATION.
3' RO = 3' REPLICATION ORGIN
TT = TRANSCRIPTION TERMINATION SEQUENCE

VIRAL AMPLIFICATION OF RECOMBINANT MESSENGER RNA IN TRANSGENIC PLANTS

This is a division, of application Ser. No. 08/176,414, filed Dec. 29, 1993, which is a continuation in part of application Ser. No. 07/997,733 filed Dec. 30, 1992, now abandoned.

BACKGROUND OF THE INVENTION

The present invention relates to the field of genetically engineering transgenic plants. More specifically, the invention relates to the use of viral RNA to achieve high level expression of foreign genes in plants.

The use of transgenic plants for high level expression of foreign genes has been targeted as an inexpensive means for mass producing desired products. All higher plants are photoautotrophic, requiring only $CO_2$, $H_2O$, $NO_3^{-1}$, $SO_4^{-2}$, $PO_4^{-3}$ and trace amounts of other elements for growth. From these inexpensive starting materials, plants are capable of synthesizing a variety of valuable products. Progress in utilizing transgenic plants as low cost factories will depend on both the characterization of biosynthetic pathways and on the further development of gene expression technologies.

In the past decade, a number of techniques have been developed to transfer genes into plants (Potrykus, I., *Annual Rev. Plant Physiol. Plant Mol. Biol.* 42:205–225 (1991)). For example, chromosomally integrated transgenes have been expressed by a variety of promoters offering developmental control of gene expression. (Walden and Schell, *Eur. J. Biochem.* 192:563–576 (1990)). This technology has been used primarily to improve certain agronomic traits such as disease resistance or food quality. (Joshi and Joshi, *Febs. Lett.* 281:1–8 (1991)). However, the utility of known transgene methodology is limited by 1) the difficulty of obtaining high level expression of individual transgenes 2) the lack of means necessary for coordinating control of several transgenes in an individual plant 3) the lack of means to enable precise temporal control of gene expression and 4) the lack of adequate means to enable shutting off introduced genes in the uninduced state (Walden and Schell, *Eur. J. Biochem* 192:563–576 (1990)).

The most highly expressed genes in plants are encoded in plant RNA viral genomes. Many RNA viruses have gene expression levels or host ranges that make them useful for development as commercial vectors. (Ahlquist, P., and Pacha, R. F., *Physiol. Plant.* 79:163–167 (1990), Joshi, R. L., and Joshi, V., *FEBS Lett.* 281:1–8 (1991), Turpen, T. H., and Dawson, W. O., Amplification, movement and expression of genes in plants by viral-based vectors, *Transgenic plants: fundamentals and applications* (A. Hiatt, ed.), Marcel Dekker, Inc., New York, pp. 195–217. (1992)). For example, tobacco (*Nicotiana tabacum*) accumulates approximately 10 mg of tobacco mosaic tombamovirus (TMV) per gram of fresh-weight tissue 7–14 days after inoculation. TMV coat protein synthesis can represent 70% of the total cellular protein synthesis and can constitute 10% of the total leaf dry weight. A single specific RNA transcript can accumulate to 10% of the total leaf mRNA. This transcript level is over two orders of magnitude higher than the transcription level observed for chromosomally integrated genes using conventional plant genetic engineering technology. This level of foreign gene expression has not yet been obtained using the prior art viral vectors in plants.

Most plant viruses contain genomes of plus sense RNA (messenger RNA polarity) (Zaitlin and Hull, *Ann. Rev. Plant Physiol.* 38:291–315 (1987)). Plus sense plant viruses are a very versatile class of viruses to develop as gene expression vectors since there are a large number of strains from some 22 plus sense viral groups which are compatible with a wide number of host plant species. (Martelli, G. P., *Plant Disease* 76:436 (1992)). In addition, an evolutionarily related RNA-dependent RNA polymerase is encoded by each of these strains. This enzyme is responsible for genome replication and mRNA synthesis resulting in some of the highest levels of gene expression known in plants.

In order to develop a plant virus as a gene vector, one must be able to manipulate molecular clones of viral genomes and retain the ability to generate infectious recombinants. The techniques required to genetically engineer RNA viruses have progressed rapidly. If the virus is an RNA virus, the virus is generally cloned as a cDNA and inserted into a plasmid. The plasmid is used to make all of the constructions. The genome of many plus sense RNA viruses can be manipulated as plasmid DNA copies and then transcribed in vitro to produce infectious RNA molecules (reviewed in Turpen and Dawson, Transgenic Plants, Fundamentals and Applications, Marcel Dekker, New York, pp 195–217 (1992)).

The interaction of plants with viruses presents unique opportunities for the production of complex molecules as typified by the TMV/tobacco system (Dawson, W. O., *Virology* 186:359–367 (1992)). Extremely high levels of viral nucleic acids and/or proteins accumulate in infected cells in a brief period of time. The virus catalyzes rapid cell-to-cell movement of its genome throughout the plant, with no significant tissue tropism. The infection is maintained throughout the life of the plant. The plants are not significantly adversely affected by the viral infection since the virus causes little or no general cytotoxicity or specific suppression of host gene expression.

The tobacco mosaic tobamovirus is of particular interest to the instant invention in light of its ability to express genes at high levels in plants. TMV is a member of the tobamovirus group. TMV virions are 300 nm×18 nm tubes with a 4 nm-diameter hollow canal, and consist of 2140 units of a single structural protein helically wound around a single RNA molecule. The genome is a 6395 base plus-sense RNA. The 5'-end is capped and the 3'-end contains a series of pseudoknots and a tRNA-like structure that will specifically accept histidine. The genomic RNA functions as mRNA for the production of proteins involved in viral replication: a 126-kDa protein that initiates 68 nucleotides from the 5'-terminus and a 183-kDa protein synthesized by readthrough of an amber termination codon approximately 10% of the time (FIG. 1). Only the 183-kDa and 126-kDa viral proteins are required for TMV replication in trans. (Ogawa, T., Watanabe, Y., Meshi, T., and Okada, Y., *Virology* 185:580–584 (1991)). Additional proteins are translated from subgenomic size mRNA produced during replication (reviewed in Dawson, W. O., *Adv. Virus Res.* 38:307–342 (1990)). The 30-kDa protein is required for cell-to-cell movement; the 17.5-kDa capsid protein is the single viral structural protein. The function of the predicted 54-kDa protein is unknown.

The minimal sequences required in cis for TMV replication are located at the extreme 5' and 3' noncoding regions (replication origins), as determined by analysis of deletion mutants in plant protoplasts (Takamatsu, N., et al., *J. Virol.* 64:3686–3693 (1990), Takamatsu, N., et al., *J. Virol.* 65:1619–1622 (1991)). In whole plants, helper-dependent RNA replicons, constructed by deletion of most of the 126/183-kDa replication protein sequence and most of the 30-kDa movement protein sequence, are replicated and spread systemically in the presence of wild type TMV (Raffo A. J., and Dawson W. O., *Virology* 184:277–289 (1991)).

Turpen, et al. discloses a simple and reliable gene transfer method wherein cDNA of TMV is engineered into *A. tumefaciens* for expression in plant cells (Turpen, T. H., Ph.D. Dissertation, University of California, Riverside, pp. 88–105 (1992)). This method provides an alternative to the use of synthetic infectious transcripts to inoculate plants based on host transcription of viral cDNA in vivo. Turpen showed successful transfection of tobacco (*N. tabacum* cv. Xanthi and Xanthi/nc) with wild type and defective viral genomes using this methodology.

Transfection also occurs spontaneously in transgenic lines containing defective or wild type cDNA of TMV integrated chromosomally (Turpen, T. H., Ph.D. Dissertation, University of California, Riverside, pp. 106–132 (1992), Yamaya, J., et al., *Mol. Gen. Genet.* 211:520–525 (1988)). Thus, once chromosomally integrated, viral replication can be derived from the process of host cell transcription.

Plant virus infections are initiated by mechanical damage to the plant cell wall. Following replication in the initially wounded cells, progeny viruses spread over short distances (cell-to-cell movement) before entering vascular tissue for long distance movement. Studies with chimeric tobamoviruses indicate that the coat protein is required for efficient long distance movement. However, a virus where the coat protein has been deleted or inactivated moves over short distances as does wild type virus (Dawson W. O. and Hilf, M. E., *Ann. Rev. Plant Physiol. Plant Mol. Biol.* 43:527–555 (1992)).

In the case of TMV, functional 30-kDa movement protein is absolutely required for cell-to-cell movement in whole plants, but can be deleted or inactivated without affecting replication in protoplasts or inoculated leaves (reviewed in Citovsky, V., Zambryski, P., *BioEssays* 13:373–379 (1991) and Deom, C. M., Lapidot, M., and Beachy, R. N., *Cell* 69:221–224 (1992)).

A sequence located within the 30kDa movement protein gene of the U1 strain of TMV serves as the origin of assembly. It is at this origin of assembly that the TMV RNA and the viral capsid protein spontaneously aggregate to initiate the assembly of virions (Butler, P. J. G., Mayo, M. A., Molecular architecture and assembly of tobacco mosaic virus particles, The molecular biology of the positive strand RNA viruses. (D. J. Rowlands, M. A. Mayo, and B. W. J. Mahy, eds.), Academic Press, London. pp. 237–257 (1987)). A functional origin of assembly is also required for efficient long distance movement (Saito, T., Yamanaka, K., and Okada, Y., *Virology* 176:329–336 (1990)). There does not appear to be any additional requirements for packaging. A variety of heterologous sequences can be encapsidated yielding rod-shaped virions whose lengths are proportional to the size of the RNA molecule containing the origin of assembly (Dawson, W. O. et al., *Virology* 172:285–292 (1989)).

Construction of plant RNA viruses for the introduction and expression of foreign genes in plants is demonstrated by French, R., et al., *Science* 231:1294–1297 (1986); Takamatsu, N., et al., *EMBO J* 6:307–311 (1987); Ahlquist, P., et al., *Viral Vectors*, Cold Spring Harbor Laboratory, New York, 183–189 (1988); Dawson, W. O., et al., *Phytopathology* 78:783–789 (1988); Dawson, W. O., et al., *Virology* 172:285–292 (1989); Cassidy, B., and Nelson, R., *Phytopathology* 80:1037 (1990); Joshi, R. L., et al., *EMBO J*. 9:2663–2669 (1990); Jupin, I., et al., *Virology* 178:273–280 (1990); Takamatsu, N., et al., *FEBS Letters* 269:73–76 (1990); Japaneses Published Application No. 63–14693 (1988); European Patent Application No. 067,553; and European Patent Application No. 194,809, European Patent Application No. 278,667. Most of the viral vectors constructed in these references were not shown to be capable of systemic movement in whole plants. Rather, gene expression has only been confirmed in inoculated leaves. In other cases, systemic movement and expression of the foreign gene by the viral vector was accompanied by rapid loss of the foreign gene sequence (Dawson, W. O., et al., *Virology* 172:285 (1989)).

With further improvements, successful vectors have been developed based on tobamoviruses for rapid gene transfer to plants. (Donson et al., *Proc. Natl. Acad. Sci.* 88:7204–7208 (1991)). For example, the α-trichosanthin gene was added to the genome of a tobamovirus vector under the transcriptional control of a subgenomic promoter obtained from a strain distantly related to wild type TMV (Turpen, T. H., Ph.D. Dissertation, University of California, Riverside, pp. 72–87 (1992)). This vector is an autonomous virus, containing all known viral functions. Two weeks post-inoculation, transfected *Nicotiana benthamiana* plants accumulated α-trichosanthin to levels of at least 2% total soluble protein. Purified recombinant α-trichosanthin produced by this method was correctly processed and had the same specific activity as the enzyme derived from the native source. Therefore, messenger RNA produced by viral RNA amplification in whole plants is fully functional. However, after prolonged replication of certain sequences using this vector, some genetic instability was observed primarily due to recombinational deletions and point mutations (Kearney, C. M., et al., *Virology* (in press)).

Recently, very similar results were obtained using gene vectors derived from additional plus sense RNA viruses infecting plants; a potyvirus, tobacco etch virus ((Dolja, V., et al., *PNAS* 89:10208–10212 (1992) and a potexvirus, potato virus X (Chapman, S., et al., Plant Journal 2:549–557 (1992)).

Therefore, the major functional disadvantages of existing prior art viral vectors are their genetic instability regarding the fidelity of maintenance of some non-viral foreign genes in systemically infected whole plants, after prolonged replication and passaging. For many products, it will be desirable to increase the genetic fidelity by lowering the proportion of deletion and other variants in amplified populations.

An additional concern regarding the use of viral vectors for the expression of foreign genes in transgenic plants is biological containment of the viral vectors encoding for foreign genes.

SUMMARY OF THE INVENTION

The present invention relates to a replicon transcribed from a transgene integrated into the chromosome of a plant cell. The replicon encodes for replication origins possessing substantial sequence identity to a plus sense, single stranded RNA plant virus and at least one gene non-native to a plus sense, single stranded RNA plant virus. However, the replicon does not encode for at least one protein necessary for replication. According to the present invention, expression of the non-native gene is regulated by a helper virus encoding for a protein needed by the replicon for replication.

According to the present invention, it is preferred that the sequence encoding the non-native gene be located 5' to the 3' replication origin of the replicon. It is further preferred that the replicon encode for a gene needed by the helper virus for systemic infection, most preferably a viral movement protein located 3' to the 5' replication origin of the replicon.

The present invention also relates to a protein expressed in a plant cell using a replicon of the present invention. The present invention also relates to an RNA sequence expressed in a plant cell using the replicon of the present invention. The present invention also relates to a primary or secondary metabolite accumulated in the tissues of a transfected plant as a result of the expression of the non-native gene encoded by a replicon of the present invention. The present invention also relates to a transgenic plant comprising a transgene integrated into the chromosome of a plant cell wherein the transgene encodes for a replicon of the present invention.

The present invention also relates to a method of expressing a gene in a plant by integrating a transgene into a chromosome of a plant cell, the transgene encoding for a replicon of the present invention. The transgenic plant is then infected with a helper virus encoding for the protein needed by the replicon for replication.

Definitions

Foreign gene: A "foreign gene" refers to any sequence that is not native to the virus.

In cis: "In cis" indicates that two sequences are positioned on the same strand of RNA or DNA.

In trans: "In trans" indicates that two sequences are positioned on different strands of RNA or DNA.

Movement protein: A "movement protein" is a noncapsid protein required for cell to cell movement of replicons or viruses in plants.

Origin of Assembly: An "origin of assembly" is a sequence where self-assembly of the viral RNA and the viral capsid protein initiates to form viriQns.

Replication origin: A "replication origin" refers to the minimal terminal sequences in linear viruses that are necessary for viral replication.

Replicon: A "replicon" is an arrangement of RNA sequences generated by transcription of a transgene that is integrated into the host DNA that is capable of replication in the presence of a helper virus. A replicon may require sequences in addition to the replication origins for efficient replication and stability.

Transcription termination region: The "transcription termination region" is a sequence that controls formation of the 3' end of the transcript. Self-cleaving ribozymes and polyadenylation sequences are examples of transcription termination sequences.

Transgene: A "transgene" refers to the DNA sequence coding for the replicon that is inserted into the host DNA.

Virion: A "virion" is a particle composed of viral RNA and viral capsid protein.

DETAILED DESCRIPTION OF THE INVENTION

The instant invention provides high level expression of foreign genes in plants by viral replicons wherein the replicons possess improved genetic stability. The replicons of the instant invention are produced in host plant cells by transcription of integrated transgenes. The replicons of the instant invention are derived, in part, from single stranded plus sense plant RNA viruses.

Figure 2A:
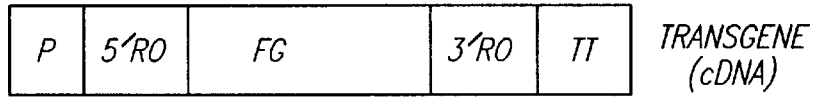
FIG. 2A–2C depict the essential features of the instantly claimed viral replicons.
Figure 2B:
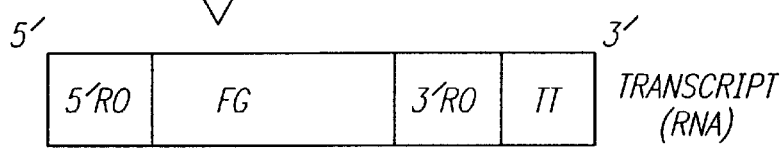
Figure 2C:
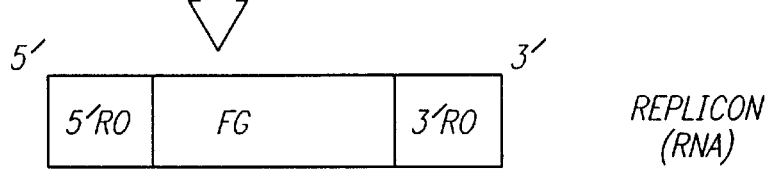

The replicons of the instant invention code for at least one foreign gene and possess sequences required in cis for replication ("replication origins"). FIG. 2(c). The replicons are produced by host cell transcription of a chromosomally integrated transgene to form an RNA transcript. The transgene is a DNA sequence that codes for the replicon and also contains a promoter and a transcription termination region. FIG. 2(a). The replicon is generated from an RNA transcript of the transgene by RNA processing and replication in the presence of a helper virus. FIG. 2(b).

The replicons of the instant invention lack functional replication protein sequences. Because the replicons of the instant invention lack replication protein sequences, they must rely on genetic complementation with helper viruses for replication. The replicon's dependency on the helper virus for replication enables regulatable amplification of these replicons through the introduction of the helper virus.

Genetic complementation of the replicon with a helper virus provides many advantages over autonomous viral vectors for amplifying gene expression. Each infected cell of a transgenic plant contains a correct master copy of the gene to be amplified. This reduces the effects of genetic drift in replicating RNA populations that can result in sequence instabilities and point mutations after prolonged replication of an RNA vector (Kearney, C. M., et al., *Virology* (in press)).

Figure 3:
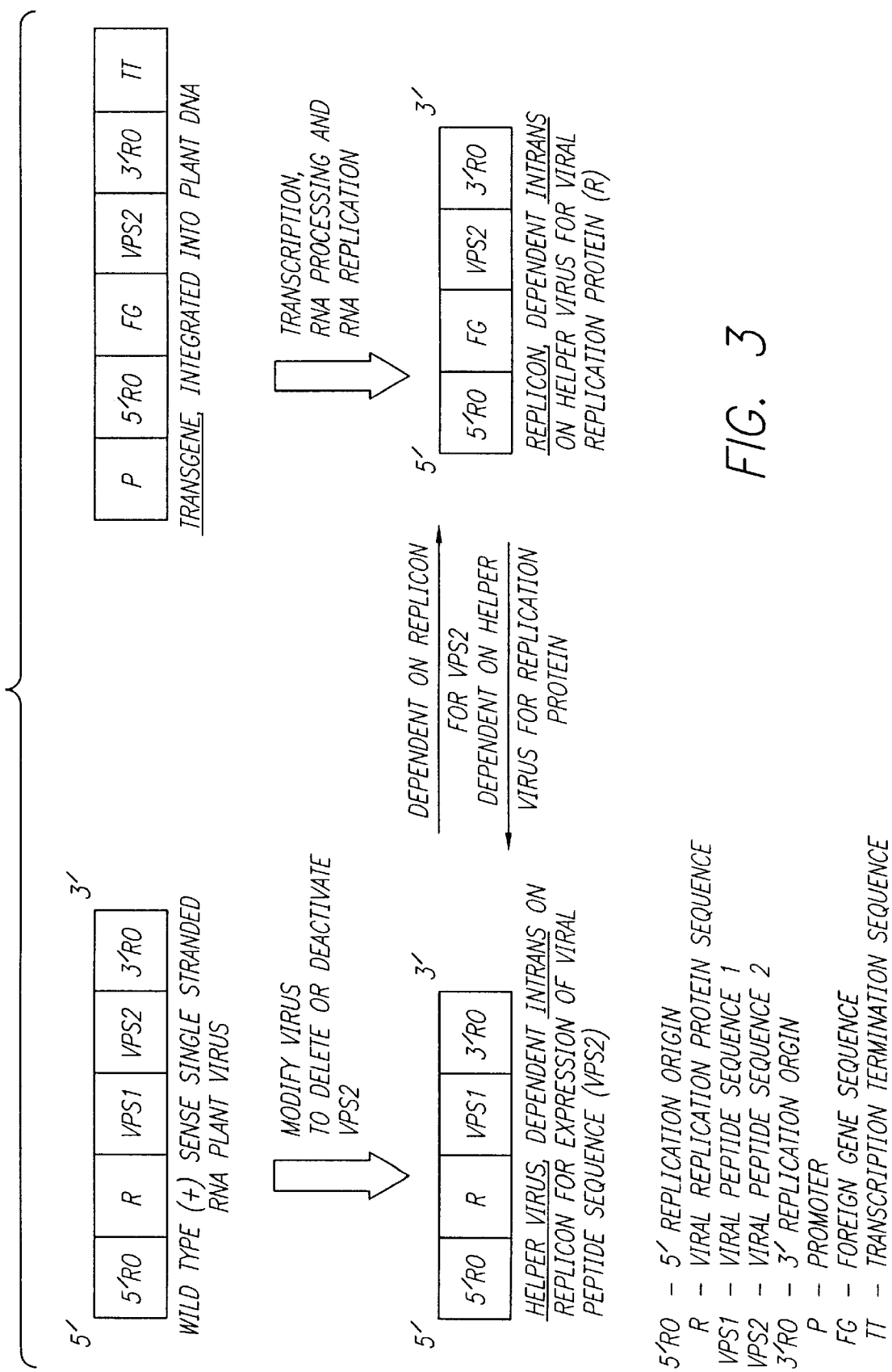
FIG. 3 depicts an embodiment where the replicon and helper virus are mutually dependent.

In a further embodiment of the instant invention, the replicon codes for at least one sequence upon which the helper virus is dependent. Thus, in this further embodiment, the replicon and the helper virus are mutually dependent. [See FIG. 3]. Helper virus dependence on the replicon insures amplified expression of the replicon sequences by the helper virus in whole plants.

In a further embodiment, the replicon codes for a functional movement protein such as the 30 kDa TMV movement protein. The helper virus used in this embodiment does not possess a functional movement protein. Thus, the helper virus is dependent on the replicon for movement functionality. Movement proteins are necessary for cell to cell movement in plants. By placing a functional movement protein sequence on the replicon and either deactivating or deleting the same sequence on the helper virus or by using a host species with helper virus encoded movement protein incompatibility, the helper virus's dependency on the replicon enables systemic infection of the whole plant with the viral replicon plus helper virus.

This embodiment of the instant invention has the further advantage that the only virus released into the environment will be a debilitated helper virus. Thus, the helper virus will not be able to spread in plants that do not already contain a functional copy of the viral movement protein. This embodiment provides an option for more stringent levels of biological containment which may be desirable in some cases for large scale commercial production.

Figure 4:
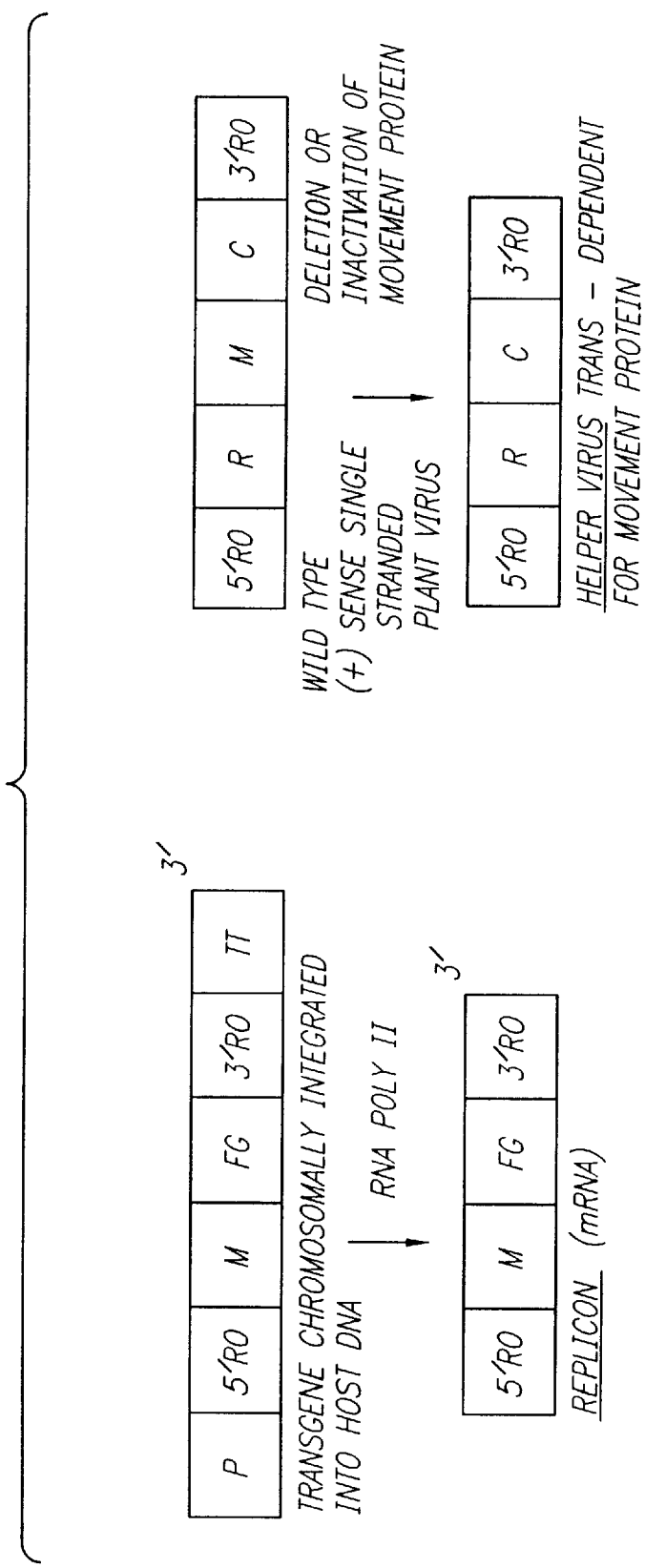
FIG. 4 depicts a preferred replicon gene arrangement where the foreign gene is situated at the 3' end of the genome 5' to the 3' replication origin.

In a preferred embodiment, the replicon is formulated such that the sequences encoding the replication origins and the movement functions are linked to the foreign gene sequences. The chromosomally integrated transgene that codes for the replicon is transcribed by host RNA polymerase II producing recombinant mRNAs. In the presence of a helper virus, these transcripts are replicated as additional replicon components in a mixed population. During viral replication, subgenomic messenger RNA may be produced from replicon RNA resulting in amplified expression of foreign genes. The most preferred replicon gene arrangement places the foreign gene at the extreme 3' end of the genome where the viral structural protein is normally encoded. See FIG. 4. This position for the foreign gene at the extreme 3' end of the genome, as depicted in FIG. 4, is critical for high level expression (Culver, J. N., et al., *Virology* (in press)). However, the protein coding sequences or other gene sequences located between the replication origins may be functional in any order.

Additional preferred embodiments of the replicon sequence include the use of regulatable promoters to control expression of the foreign gene and/or movement protein. One promoter for expression of a fusion protein containing the foreign protein or a series of subgenomic promoters may be employed. Self-cleaving ribozymes or a polyadenylation region may also be employed as the transcription termination regions.

The replicons are generated in vivo in plants through transcription of transgenes that are integrated into the host plant cell chromosome and through replication in the presence of a helper virus. The transgenes can be introduced into the host plant cell chromosome by known transformation methods using a variety of promoters. After the replicon has been introduced into the host, the resulting transgenic plants are grown to an optimized stage at which point a helper virus strain is added. The replicons are then amplified by the introduced helper virus and the foreign gene is expressed.

The foreign gene product coded for and expressed by the replicon can be a very wide variety of RNA or proteins products and include, for example, antisense and ribozyme RNA, regulatory enzymes, and structural, regulatory and therapeutic proteins that may be expressed in their native form or as gene fusions. Typical therapeutic proteins include members of the interleukin family of proteins and colony stimulating factors such as CSF-G, CSF-GM and CSF-M. It is understood, however, that any therapeutic protein can be coded for and expressed in the instant invention.

If expression of the foreign gene results in the accumulation of a protein or other material in the plant tissues, that resulting product may be harvested once the desired concentration of that product is achieved. Significant quantities of recombinant proteins, nucleic acids or other metabolites can be inexpensively produced using this procedure. The low level of expression and wide variation that is observed in transgenic organisms chromosomally transformed with the same construct (a phenomenon attributed to "position effects"), is avoided by this method. RNA-based amplification is not critically dependent on initial transcript amounts. There is also no theoretical limit to the number of genes that can be amplified at the RNA level. The target gene remains "off" before amplification because subgenomic mRNA is only produced during viral replication. Therefore this approach might be particularly appropriate for controlling complex biochemical pathways or producing products that are toxic to the plant. It would be feasible for example, to overexpress critical enzymes in a pathway and simultaneously down-regulate other genes by amplifying antisense RNA only after inoculation with a helper virus. These types of manipulations are not possible using existing or proposed technologies for chromosomal transformation of plants or plant cell cultures or by using prior art viral vectors.

DESCRIPTION OF THE PREFERRED EMBODIMENTS

The following examples further illustrate the present invention.

EXAMPLE 1

Construction of a Transgene for Expression of Recombinant Messenger RNA

Figure 1:
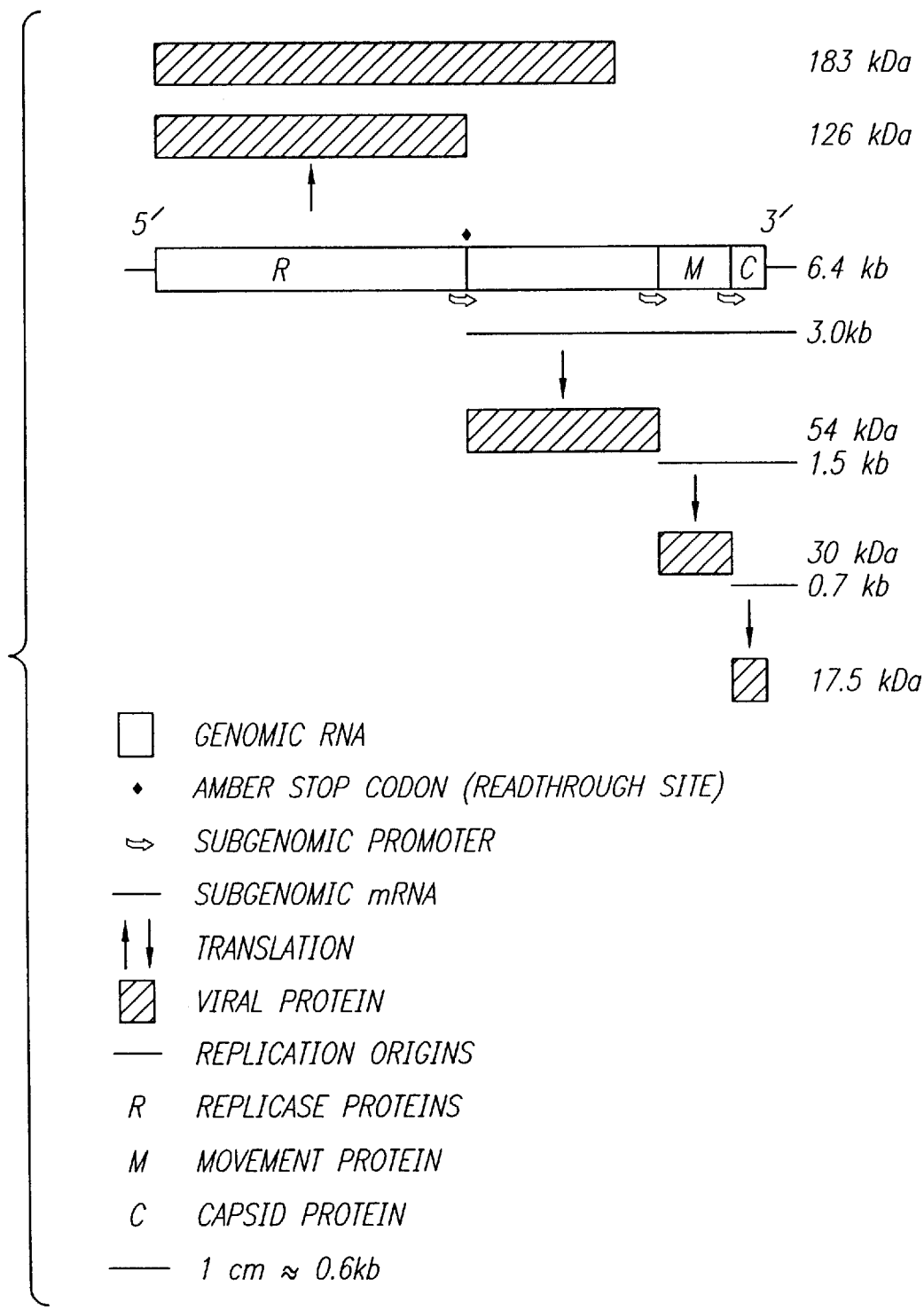
FIG. 1 depicts the genome of wild type TMV.

Construction of a transgene derived from TMV is set forth herein. The wild type TMV genome is set forth in FIG. 1. The construction of DNA plasmids containing the 5' replication origin fused to the CaMV 35S promoter are described in (Ow, D. W., et al., *Science* 234:856–859 (1986)) and the 3' replication origin fused to a ribozyme termination region are described by Turpen, T. H., Ph.D. Disertation, University of California, Riverside, pp. 88–105 (1992).

The substitution of the coat protein gene for the coding sequence of CAT is described in Dawson, et al., *Phytopathol.* 78:783–789 (1988).

Figure 5:
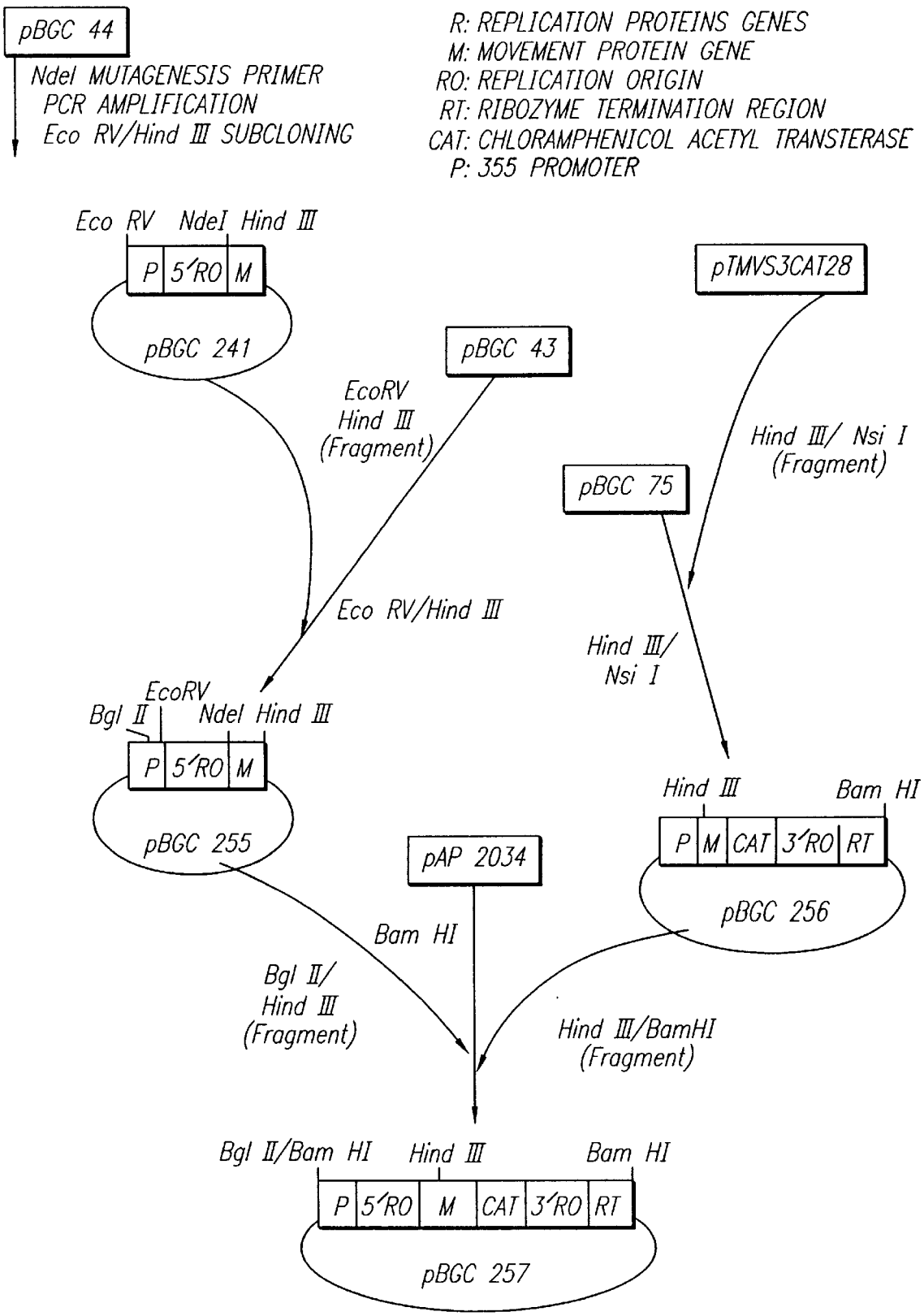
FIG. 5 depicts the construction of a transgene for the synthesis of a replicon encoding Chloramphenicol Acetyltransferase (CAT) in an Agrobacterium transformation vector.

Previously disclosed plasmids, pBGC43, pBGC44, pBGC75 (Turpen, T. H., Ph.D. Disertation, University of California, Riverside, pp. 88–136 (1992)). and pTMVS3CAT28 (Dawson, et al., *Phytopathol.* 78:783–789 (1988)) are used as precursors for the construction of the desired transgene for synthesis of replicon RNA (FIG. 5). Construction of plasmids pBGC43, pBGC44, pBGC75 are described in Table 1 taken from Turpen, T. H., Ph.D. Disertation, University of California, Riverside, pp. 92, 112 (1992). Construction of plasmids pBGC43, pBGC44, pBGC75 and pTMVS3CAT28 are also discussed below.

Preparation of pTMVS3-CAT-28 pTMVS3-CAT-28 containing a substitution of the chloramphenicol acetlytransferase (CAT) gene for the coat protein gene was constructed as follows. The CAT gene was removed from pCM1 (Pharmacia) with SalI and ligated into XhoI-cleaved pTMVS3-28. pTMVS3-28 was constructed by cloning genomic length TMV cDNA (6.4 kb) in pBR322 as described in Dawson W., et al., *Proc. Natl. Acad. Sci.* 83:1832–36, (1986). The CAT construction produced pTMVS3-CAT-28 from which the mutant cp S3-CAT-28 was transcribed. Correct sequence and orientation were confirmed by sequencing. *Gene Anal. Technol.* 2:89–94.

Preparation of pBGC43 pTK49 was constructed by cloning the 1.4 kb PstI-HindIII fragment of TMV cDNA in pUC19 as described by Dawson, W., et al., *Proc. Natl. Acad. Sci.* 83:1832–36 (1986). The 1.4 kb PstI-HindIII from pTK49 was recloned into pUC19 to form pTT1. The 1.6 kb HindIII-BamHI fragment from pDO432 described in Ow et al., *Science* 234:856–59, (1986) was cloned into pTT1. NotI linkers were added at the HindIII site of the fragment and the EcoRI site of the vector. pTT3 was constructed by digesting pTT2 with PstI-BamHI and mung bean nuclease to position the 35S promoter at the 5' end of TMV cDNA. The 1.9 kb NotI-SmaI fragment of pTT3 was cloned into pBStKs+ to form pBGC43.

Preparation of pBGC44

The 1.4 kb SalI-HindIII fragment from pTT1 was cloned into pstSk- to form pBGC8. The 3.6 kb HindIII fragment from pTMV204 disclosed in Dawson, et al., *Proc. Natl.*

Acad. Sci. 83:1832–36, (1986) was cloned into pBGC8 to form pBGC9. The 4.8 kb SmaI-PstI fragment from pBGC9 was cloned into pBGC43 (described above) to form pBGC44.

Preparation of pBGC 75

The 2.1 kb EcoRI-PstI fragment from pTMV204 described in Dawson, W., et al., *Proc. Natl. Acad. Sci.* 83:1832–36, (1986) was cloned into pBstSk- to form pBGC11. The 3.6 HindIII fragment from pTMV204 was cloned into pBGC11 to form pBGC14. The 0.4 kb NcoI-PstI fragment of pTMVcpS3-28 (0.5 kb coat protein deletion of pTMV304, described in Dawson, W., et al. *Phytopathology* 78:783–789) was substituted for the 0.9 kb NcoI-PstI fragment of pGC14 to form pGC15. pBGC19 was formed by deleting the 0.03 kb KpnI-HindIII polylinker region of pBGC14.

pBGC70 was formed by cloning a 0.05 kb synthetic ApaI-PstI ribozyme encoding fragment into pBstSk+. pBGC72 was formed by deleting the 3.5 kb ClaI fragment from pBGC19. pBGC73 was formed by cloning the 0.05 kb ApaI-PstI fragment of pBGC70 into pBGC72. pBGC74 was formed by substituting the 0.1 kb ClaI-NsiI fragment of pBGC15 for the 0.5 kb ClaI-NsiI fragment of pBGC73. The 3.5 kb ClaI fragment of pBGC19 was cloned into pBGC74 to form pBGC75.

TABLE 1

PATENT

| Designation | Relevant Characteristics | Source or Reference |
|---|---|---|
| *E. coli* | | |
| JM109 | recA1, endA1, gyrA96, thi-, hsdR17($r_{K-}$, $m_{K+}$), supE44, relAl, A(kac-proAB), [F traD36, proAB, lacI$^q$ZΔM15] | Yanish-Perron et al. Gene 33:103–199 (1985) |
| HB101 | hsdS20($r_{B-}$, $m_{B-}$), supE44, ara14, gelK2, lecY1, proA2, rspL20, xyl-5, mtl-1 recA13 | Sambrook et al. Molecular Cloning: A Laboratory Manual Cold Spring Harbor Laboratory (1989) |
| GJ23 | General plasmid mobilizing strain containing pGJ28 and pR64drd11 | Van Raute et al. EMBO J. 2:411–417 (1983) |
| *A. tumefaciens* | | |
| C58C1 | Rif$^r$ derivative of strain C58 containing pGV3850 | Zambryski et al. EMBO J. 2:2143–2150 (1983) |
| A. t.-17 | TMV transfection strain containing pGV3850::pBGC17 | Turpen, T.H., Ph.D. Dissertation, University of California, Riverside, pp. 106–132 (1992) |
| A. t.-46 | TMV transfection strain containing pGV3850::pBGC46 | Turpen, T.H., Ph.D. Dissertation, University of California, Riverside, pp. 106–132 (1992) |
| A. t.-49 | TMV transfection strain containing pGV3850::pBGC49 | Turpen, T.H., Ph.D. 132 (1992) |
| A. t.-77 | TMV transfection strain containing pGV3850::pBGC77 | Turpen, T.H., Ph.D. Dissertation, University of California, Riverside, pp. 88–105 (1992) |
| Plasmids | | |
| pBstSk/pBstKS | *E. coli* cloning plasmids, pBluescript (+/-) | Stratagene, La Jolla, California |
| pUC18/pUC19 | *E. coli* cloning plasmids | Yanish-Perron et al. Gene 33:103–199 (1985) |
| pT7/T3α19 | *E. coli* cloning plasmid | BRL, Gaithersburg, MD |
| pTK49 | 1.4 kb PstI-HindIII fragment of TMV cDNA in pUC19 | Dawson et al. Proc. Natl. Acad. Sci. U.S.A. 83:1832–1836 (1986) |
| pTMV204 | Genomic length TMV cDNA (6.4 kb) in pBR322 | Dawson, et al. Proc. Natl. Acad. Sci. U.S.A. 83:1832–1836 (1986) |
| pTMV212 | Genomic length TMV cDNA in pT7/T3α19 | Dawson, unpublished |
| pTMVcpS3-28 | Coat protein deletion (0.5 kb) mutant of pTMV204 | Dawson et al. Phytopathology 78:783–789 (1988) |
| pAP2034 | pBR322-_sed selection-expression vector for plant transformation, Cb$^r$, Sp$^r$, Kn$^r$ | Velton et al. Nucleic Acids Res. 13:6981–6998 (1985) |
| pDO432 | Source of restriction site modified 35S promoter | Ow et al. Science 234:856–859 (1986) |
| pTT1 | 1.4 kb PstI-HindIII fragment from pTK49 cloned in pUC19 | Turpen, T.H., Ph.D. Dissertation, University of California, Riverside, pp. 106–132 (1992) |
| pTT2 | 1.6 kb HindIII-bamHI fragment from pDO432 cloned in pTT1, NotI linkers added at KindIII site of fragment and EcoRI site of vector | Turpen, T.H., Ph.D. Dissertation, University of California, Riverside, pp. 106–132 (1992) |
| pTT3 | PstI-BamHI + mung bean nuclease deletion of PTT2 positioning 35S promoter at 5'-end of TMV cDNA | Turpen, T.H., Ph.D. Dissertation, University of California, Riverside, pp. 106–132 (1992) |

TABLE 1-continued

PATENT

| Designation | Relevant Characteristics | Source or Reference |
|---|---|---|
| pBGC6 | 0.2 kb XhoI-PstI fragment from pTMVcpS3-28 in pBstKS+ | Turpen, T.H., Ph.D. Dissertation, University of California, Riverside, pp. 106–132 (1992) |
| pBGC8 | 1.4 kb SalI-HindIII fragment from PTT1 cloned in pBstSK- | Turpen, T.H., Ph.D. Dissertation, University of California, Riverside, pp. 106–132 (1992) |
| pBGC9 | 3.6 kb HindIII fragment from pTMV204 cloned in pBGC8 | Turpen, T.H., Ph.D. Dissertation, University of California, Riverside, pp. 106–132 (1992) |
| pBGC11 | 2.1 kb EcoRI-PstI fragment from pTMV204 cloned in pBstSK- | Turpen, T.H., Ph.D. Dissertation, University of California, Riverside, pp. 106–132 (1992) |
| pBGC14 | 3.6 kb HindIII fragment from pTMV204 cloned in pBGC11 | Turpen, T.H., Ph.D. Dissertation, University of California, Riverside, pp. 106–132 (1992) |
| pBGC15 | 0.4 kb NcoI-PstI of pTMVcpS3-28 substituted for 0.9 kb NcoI-PstI fragment of pBGC14 | Turpen, T.H., Ph.D. Dissertation, University of California, Riverside, pp. 88–105 (1992) |
| pBGC16 | 3.3 kb SalI-BamHI fragment of pBGC9 cloned in pAP2034 | Turpen, T.H., Ph.D. Dissertation, University of California, Riverside, pp. 106–132 (1992) |
| pBGC17 | Full length wtTMV cDNA in pAP2034 | Turpen, T.H., Ph.D. Dissertation, University of California, Riverside, pp. 106–132 (1992) |
| pBGC19 | 0.03 kb KpnI-HindIII polylinker deletion of pBGC14 | Turpen, T.H., Ph.D. Dissertation, University of California, Riverside, pp. 106–132 (1992) |
| pBGC43 | 1.9 kb NotI-SmaI fragment from pTT3 cloned in pBstKS+ | Turpen, T.H., Ph.D. Dissertation, University of California, Riverside, pp. 106–132 (1992) |
| pBGC44 | 4.8 kb SmaI-PstI fragment of pBGC9 cloned in pBGC43 | Turpen, T.H., Ph.D. Dissertation, University of California, Riverside, pp. 106–132 (1992) |
| pBGC45 | 4.3 kb BglII-BamHI fragment of pBGC44 cloned in the BamHI site of pAP2034 | Turpen, T.H., Ph.D. Dissertation, University of California, Riverside, pp. 106–132 (1992) |
| pBGC46 | 3.1 kb BamHI fragment of pBGC44 cloned in the BamHI site of pAP2043 | Turpen, T.H., Ph.D. Dissertation, University of California, Riverside, pp. 106–132 (1992) |
| pBGC49 | 2.6 kb BamHI fragment of pBGC14 cloned in the BamHI site of pBGC45 | Turpen, T.H., Ph.D. Dissertation, University of California, Riverside, pp. 106–132 (1992) |
| pBGC70 | 0.05 kb synthetic ApaI-PstI ribozyme encoding fragment cloned in pBstSK+ | Turpen, T.H., Ph.D. Dissertation, University of California, Riverside, pp. 88–105 (1992) |
| pBGC72 | 3.5 kb ClaI deletion of pBGC19 | Turpen, T.H., Ph.D. Dissertation, University of California, Riverside, pp. 88–105 (1992) |
| pBGC73 | 0.05 kb ApaI-PstL fragment of pBGC70 cloned in pBGC72 | Turpen, T.H., Ph.D. Dissertation, University of California, Riverside, pp. 88–105 (1992) |
| pBGC74 | 0.1 kb ClaI-NsiI fragment of pBGC15 substituted for 0.5 kb ClaI-Nsil gragment of pBGC73 | Turpen, T.H., Ph.D. Dissertation, University of California, Riverside, pp. 88–105 (1992) |
| pBGC75 | 3.5 kb ClaI fragment of pBGC19 cloned into pBGC74 | Turpen, T.H., Ph.D. Dissertation, University of California, Riverside, pp. 88– |

TABLE 1-continued

| PATENT | | |
|---|---|---|
| Designation | Relevant Characteristics | Source or Reference |
| | | 105 (1992) |
| pBGC77 | 2.7 kb BamHI fragment of pBGC75 cloned into pBGC45, 35S promoter plus full length cp-TMV cDNA in pAP2034 with rebozyme self-cleaving fragment at 3'-terminus | Turpen, T.H., Ph.D. Dissertation, University of California, Riverside, pp. 88–105 (1992) |

With regard to construction of the transgene, it is desired to place the 30-kDA movement protein gene at precisely the same position as the replicase gene (relative to 5' replication origin in the wild type TMV genome, See FIG. 5). To accomplish this, a NdeI site is introduced at the start codon of each gene by PCR-based mutagenesis using synthetic primers and unique adjacent cloning sites. A 270 bp mutagenesis product containing the internal NdeI site from the PCR primer is subcloned using the EcoRV site in the cauliflower mosaic virus 35S promoter and the HindIII site in the 30-kDa protein gene. The ligation product is then sequence verified.

The 3' segment of the replicon, containing the CAT gene will be placed adjacent to the 3'-ribozyme as a HindIII-NsiI fragment from the transient TMV vector pTMVS3CAT28 (FIG. 5). In the final cloning step, the 5' portion of the transgene and the 3' portion will be subcloned into the unique BamHI site of the plant transformation vector pAP2034 (Velton and Schell, *NAR* 13:6981–6998 (1985) as a Bg1II-BamHI fragment described previously (Turpen, T. H., Ph.D. Disertation, University of California, Riverside, pp. 88–132 (1992)). The nucleotide sequence of the replicon RNA, produced by host transcription, RNA processing, and replication in the presence of a helper virus is given as SEQ ID NO:1, and its amino acid sequence as SEQ ID NO:2 and SEQ ID NO:3. Thus, the foreign gene (CAT) is placed on a RNA viral replicon, under control of the coat protein subgenomic promoter for messenger RNA synthesis (located at the 3' end of the movement protein gene).

EXAMPLE 2

Transformation of Plants.

In one embodiment of this invention, *Agrobacterium tumefaciens* is used for insertion of this sequence into the plant chromosome as described previously (Turpen, T. H., Ph.D. Dissertation, University of California, Riverside, pp. 106–132 (1992)). The transformation vector pAP2034 is a cointegrating type Agrobacterium vector. pAP2034 containing the transcription unit for the production of replicon RNA is mobilized into *A. tumefaciens* by conjugation using the helper strain GJ23 (Van Haute, E., Joos, et al., *EMBO J.* 2:411–417 (1983)). Transconjugants are selected and the structure of the cointegrate between donor plasmid and the disarmed Ti plasmid pGV3850 (Zambryski, P., et al., *EMBO J.* 2:2143–2150 (1983)) is confirmed by Southern blot hybridization. A correct homologous recombination event places the transgene construct between the T-DNA borders.

Axenic leaf segments of *N. tabacum* cv. Xanthi are treated (Horsch, R. B., et al., Leaf disc transformation, *Plant molecular biology manual*. (S. B. Gelvin, R. A. Schilperoort, and D. P. S. Verma, eds.), Kluwer Academic Publishers, Dordrecht, The Netherlands, pp. A5:1–9 (1988)) in the following sequence: day 1; leaf segments are dipped in *A. tumefaciens* liquid culture and placed on regeneration media (RM), day 3; explants are transferred.to RM supplemented with cefotaxime (500 μg/ml), day 5; explants are transferred to RM/cefotaxime (500 μg/ml)+kanamycin (100 μg/ml), day 30–40; shoots excised and placed onto rooting media containing cefotaxime (500 μg/ml) and kanamycin (100 μg/ml). Cultures are maintained under continuous fluorescent light (Sylvania GTE, Gro-Lux WS) at 20° C.

Hardened plants are grown in commercial potting soil (Cascade Forest Products Inc., Arcata, Calif.) at a temperature of 21°–29° C., with a controlled release fertilizer (Osmocote, 14-14-14) using natural light (Vacaville, Calif.) supplemented with fluorescent light on a 16 hr day length in an indoor greenhouse. The antibiotic resistance trait carried in transgenic lines is scored by germinating seedlings in sterile agar in the presence of 100 ug/ml kanamycin (Dunsmuir, P., et al., Stability of introduced genes and stability of expression, *Plant molecular biology manual*. (S. B. Gelvin, R. A. Schilperoort, and D. P. S. Verma, eds.), Kluwer Academic Publishers, Dordrecht, The Netherlands, pp. C1:1–17 (1988)).

EXAMPLE 3

Production of Replicon RNA in the Presence of Helper Virus.

The nucleotide sequence of the replicon RNA, produced by host transcription, RNA processing, and replication in the presence of a helper virus, is given as SEQ ID NO:1, and its amino acid sequence as SEQ ID NO:2 and SEQ ID NO:3. Tobamoviruses with mutations or naturally occurring variation in the 30-kDa protein gene are deficient in cell-to-cell movement on specific host species. Transgenic plants or alternate hosts can complement this defect. It will be appreciated to those skilled in the art that there are numerous methods of producing helper tobamoviruses by genetic engineering or by mutagenesis in addition to those helper variants or host species combinations occurring naturally. Likewise, methods for producing transgenic plants which express 30 kDa protein and which complement defective 30 kDa containing viruses have been published. For example, movement deficient helper viruses can be synthesized by transcription of TMV with known mutations for the production of RNA inoculum. Transgenic plants expressing the 30-kDa protein complement this defect (Deom, C. M., et al., *Science* 237:389–394 (1987)). Therefore, large quantities of a helper virus can be propagated. In one embodiment of this invention, a 30-kDa protein frameshift mutant, having a single base pair deletion at position 4931 thereby creating a EcoRV site in the cDNA, is used as helper virus. Transgenic tobacco (~100 plants) are regenerated containing this replicon transgene construction and assayed for CAT activity in the presence and absence of helper viruses using procedures described (Shaw, W. V., Chloramphenicol acetyltransferase from chloramphenicol-resistant bacteria, *Methods in Enzymology*, Vol. 53, (S. Fleischer and L. Packer, eds.), pp. 737–755 (1975)). 200 mg of leaf tissue is macerated in assay buffer followed by the addition of 0.5 mM acetyl CoA and 0.1 uCi [$^{14}$C] chloramphenicol, incubation for 45 min at 37° C., extraction, resolution by thin-layer chromatography, and autoradiography.

EXAMPLE 4
Production of CAT in Tobacco Plants Using a Replicon RNA in the Presence of Helper Virus.

Several tobacco plants (*Nicotiana tabacum*) were transformed with a transgene of the present invention in order to evaluate the ability of the transgene to be expressed within a plant cell as well as the ability of the transgene to systemically infect a plant and express a protein encoded by the transgene. In the present example, systemic expression of chloramphenicol acetyl transferase encoded by the transgene was achieved at a level two fold that of the background level and comparable to levels obtained for single copy tobacco genes.

Figure 6:
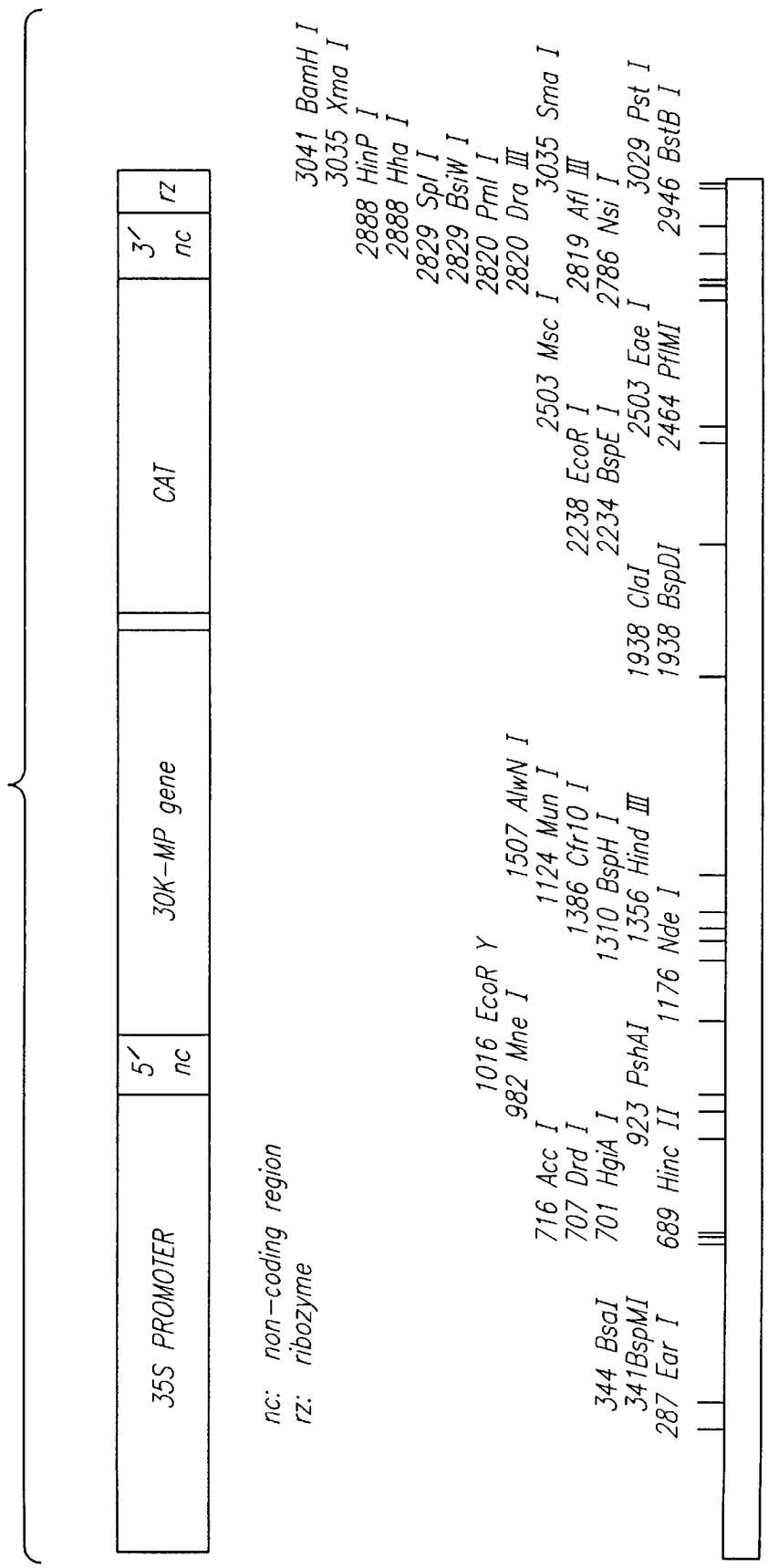
FIG. 6 provides a restriction map of the transgene portion of pBGC272.

In the present example, pBGC272 and pBGC273 were used to introduce the transgenes. A restriction map of the transgene portion of pBGC272 is provided in FIG. 6. pBGC272 has been deposited with the American Type Culture Collection, Rockville, Md. (ATCC) under Accession No. 7532. It is predicted that amplified expression of CAT from pBGC272 would be observed in the presence of a helper virus through complementation with the helper virus.

A control plasmid, pBGC273, was also prepared which differs from pBGC272 in that the 3' noncoding region has been deleted. Amplified expression of CAT is not expected with pBGC273 because deletion of the 3' noncoding region prevents synthesis of the minus strand.

Identification of Transcript Production

Tobacco plants were transformed with either pBGC272 or pBGC273 using the *Agrobacterium tumefaciens* leaf-dip method as described in Example 2. In order to save time, bacterial conjugation was avoided by using a binary plasmid vector system for plant transformation instead of employing cointegrate vectors. Bevan, M., et al. *Nucleic Acid Res.* 12:8711–8721 (1984).

Figure 7:
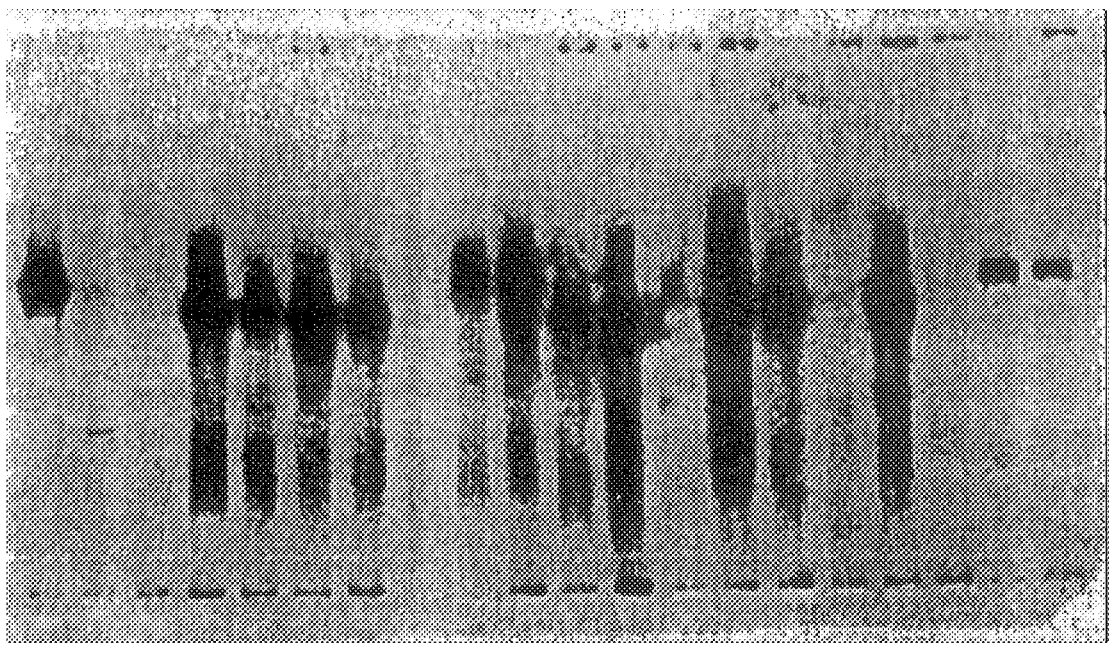
FIG. 7 depicts an autoradiograph showing the separation and identification of pBGC272 and pBGC273.

The presence of the viral transcripts after inoculation was measured by northern hybridization. Specifically, total RNA was purified, glyoxalated, separated by electrophoresis, blotted to a nylon membrane (Nytran) and probed with the NdeI-NsiI fragment of pBGC272 which had been $^{32}$P-labeled by the random primer method. An autoradiograph showing the separation and identification of pBGC272 and pBGC273 is depicted in FIG. 7. Lanes 1, 2 and 20 contain control DNA restriction fragments from pBGC272. Lanes 3–10 and 13–18 contain total RNA from transgenic plant samples (pBGC272, pBGC273). Lanes 11 and 12 contain control samples from 30K transgenic plants (line 26C) known to complement helper virus TMMVDEcoRV. Lane 19 contains RNA (1/220 equivalent) from helper virus TMMVDEcoRV-infected line 26C control plants.

Out of 16 plants transformed with pBGC272, 12 contained abundant levels of transcript. Similarly, out of 6 plants transformed with pBGC273, 4 plants produced transcripts.

Identification of CAT Production

The ability of pBGC272 to systemically infect a plant and produce a marker protein, chloramphenicol acetyl transferase (CAT), was also evaluated. CAT concentrations were determined using an ELISA assay. Gendloff, E., et al. *Plant Mol. Biol.* 14:575–583 (1990). Leaf disc samples (#8 core bore) were used. Total soluble protein from the same leaf disk samples used for CAT/ELISA was determined by the method Bradford, M. *Anal. Biochem.* 72:248–254 (1976).

Three groups of plants containing pBGC272 or pBGC273 by the *Agrobacterium tumefaciens* leaf-dip method were infected with one of three helper viruses. The helper viruses used in the present example include the wild type TMV virus (TMVU1), TMVDEcoRV and TMV30K-O. The helper viruses used in the present study are derived from the readily available tobamovirus strains, TMVU1 (also known as the common or wild type strain, ATCC No. PV 135) and odonoglossum ringspot tobamovirus (ORSV, ATCC No. PV274). Paul, H., C.M.I./A.A.B. Descriptions of Plant Viruses, No. 155 (TMVU1); Zaitlin, M., C.M.I./A.A.B. Descriptions of Plant Viruses, No. 151 (ORSV).

Helper virus TMVDEcoRV contains a point mutation in the TMV 30K gene. TMVDEcoRV was created by deleting nucleotide 4931 by oligonucleotide site directed mutagenesis of TMVU1 cDNA, thereby introducing an EcoRV site at this position and causing a frame shift mutation in the 30K gene. Infectious RNA transcripts are then synthesized in vitro and used as inoculum.

TMV30K-O contains the 30K gene from odonoglossum ringspot tobamovirus (ORSV) in a U1 strain background. TMV30K-O is partially deficient in movement function, showing delated and sporadic systemic infection in Xanthi tobacco. DawsQn, W., et al. *Ann. Rev. Plant Physiol. Plant Mol. Biol.* 43:527–555 (1992). Helper virus TMV30K-O may be prepared by substituting the cDNA encoding the 30K gene of the TMVU1 strain with the 30K gene from ORSV by routine genetic manipulation techniques. Infectious RNA transcripts are then synthesized in vitro and used as inoculum.

The first group of plants (147 individuals) were infected with TMVDEcoRV. Plants containing pBGC272 did not show symptoms of systemic infection and were thus unable to complement the helper virus or amplify CAT expression.

The second group of plants (9 individuals) were infected with TMVU1. These plants exhibited systemic infection of the wild type virus but were unable to amplify CAT expression above background control levels because genetic complementation is not necessary for systemic infection of the plant with a wild type helper virus.

The third group of plants (78 individuals) were infected with TMV30K-0. Of the 78 inoculated plants, 24 individuals became systemically infected earlier than plants inoculated solely with TMV30K, indicating complementation of the movement function debilitated helper virus with pBGC272.

Of the 24 systemically infected plants, 19 plants had been infected with pBGC272 and 5 with pBGC273. Of the 19 plants infected with pBGC272, 12 were found to contain elevated levels of CAT. Upon resampling and assaying in triplicate, 8 plants were found to have CAT levels of roughly 0.1 ng CAT/mg of total soluble protein which is two fold that of the background level.

Biological Deposits

The following plasmids have been deposited at the American Type Culture Collection (ATCC), Rockville, Md., USA, under the terms of the Budapest Treaty on the International Recognition of the Deposit of Microorganisms for the Purposes of Patent Procedure and Regulations thereunder (Budapest Treaty) and are thus maintained and made available according to the terms of the Budapest Treaty. Availability of such plasmids is not to be construed as a license to practice the invention in contravention of the rights granted under the authority of any government in accordance with its patent laws.

The deposited cultures have been assigned the indicated ATCC deposit numbers:

| Plasmid | ATCC No. |
|---------|----------|
| pBGC272 | No. 75632 |

Pursuant to 37 C.F.R. §1.808, Applicants agree that all restrictions imposed by the depositor on the availability to the public of the deposited plasmids will be irrevocably removed upon the granting of a patent on the present application.

While the invention of this patent application is disclosed by reference to the details of preferred embodiments of the invention, it is to be understood that this disclosure is intended in an illustrative rather than limiting sense, as it is contemplated that modifications will readily occur to those skilled in the art, within the spirit of the invention and the scope of the appended claims. It is further understood that the instant invention applies to all viruses infecting plants and plants generally and is not limited to those plasmids, viruses or plants described herein.

What is claimed is:

1. A system comprising:
   (a) a replicon comprising:
      (i) a plus sense, single stranded RNA plant virus replication origin,
      (ii) at least one gene non-native to a plus sense, single stranded RNA plant virus,
      the replicon not encoding for at least a plus sense, single stranded RNA plant virus replicase, and
   (b) a helper virus which is a plus sense, single stranded RNA plant virus comprising:
      at least a plus sense, single stranded RNA plant virus replicase gene, and
      the helper virus not encoding at least a plus sense, single stranded RNA plant virus movement protein,
   wherein the replicon further encodes at least a plus sense, single stranded RNA plant virus movement protein, and
   wherein a DNA sequence of the replicon is integrated as a transgene in the chromosome of a plant cell, suitable as a host for the replicon.

2. The system of claim 1, wherein the sequence encoding the non-native gene in the replicon is located 5' to the 37' replication origin of the replicon.

3. The system of claim 1, wherein the viral movement protein is native to a tobamovirus.

4. The system of claim 3, wherein the DNA encoding the tobamovirus movement protein is located 3' to the 5' replication origin of the replicon.

5. The system of claim 1, wherein the viral movement protein is native to a TMV.

6. The system of claim 5, wherein the DNA encoding the TMV movement protein is located 3' to the 5' replication origin of the replicon.

7. The system of claim 1, wherein the non-native gene is expressed systemically in the presence of the helper virus.

8. The system of claim 3, wherein the non-native gene is expressed systemically in the presence of the helper virus.

9. A transgenic plant containing a system comprising:
   a replicon comprising:
      (i) a plus sense, single stranded RNA plant virus replication origin,
      (ii) at least one gene non-native to a plus sense, single stranded RNA plant virus,
      the replicon not encoding for at least a plus sense, single stranded RNA plant virus replicase, and
   a helper virus which is a plus sense, single stranded RNA plant virus comprising:

at least a plus sense, single stranded RNA plant virus replicase gene, and the helper virus not encoding at least a plus sense, single stranded RNA plant virus movement protein, wherein the replicon further encodes at least a plus sense, single stranded RNA plant virus movement protein, and wherein the replicon is integrated as a transgene in the chromosome of a plant cell, suitable as a host for the replicon.

10. A method for expressing a protein in plants comprising:

(a) integrating a transgene into a chromosome of a plant cell, the transgene ending for a replicon comprising:

(i) a plus sense, single stranded RNA plant virus replication origin, (ii) at least one gene non-native to a plus sense, single stranded RNA plant virus, the replicon not encoding for at least a plus sense, single stranded RNA plant virus replicase, and (b) infecting the plant cell with a helper virus which is a plus sense, single stranded RNA plant virus, the helper virus comprising:

at least a plus sense, single stranded RNA plant virus replicase gene, and the helper virus not encoding at least a plus sense, single stranded RNA plant virus movement protein, wherein the replicon further encodes at least a plus sense, single stranded RNA plant virus movement protein.

11. A method of claim 10, wherein the movement protein is native to tobamovirus.

12. A method of claim 10, wherein the movement protein is native to TMV.

13. An RNA composition comprising a replicon RNA transcript and a helper virus RNA transcript expressed in a plant cell using the system of claim 1.

14. An RNA composition comprising a replicon RNA transcript and a helper virus RNA transcript expressed in a plant cell using the system of claim 3.

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 1825 base pairs
        ( B ) TYPE: nucleic acid
        ( C ) STRANDEDNESS: unknown
        ( D ) TOPOLOGY: unknown ( i i ) MOLECULE TYPE: RNA (genomic)

( i x ) FEATURE:
        ( A ) NAME/KEY: CDS
        ( B ) LOCATION: 70..1527

( x i ) SEQUENCE DESCRIPTION: SEQ ID NO:1:

```
GUAUUUUUAC  AACAAUUACC  AACAACAACA  AACAACAAAC  AACAUUACAA  UUACUAUUUA                60

CAAUUACAU  AUG  GCU  CUA  GUU  GUU  AAA  GGA  AAA  GUG  AAU  AUC  AAU  GAG           108
           Met  Ala  Leu  Val  Val  Lys  Gly  Lys  Val  Asn  Ile  Asn  Glu
            1              5                        10

UUU  AUC  GAC  CUG  ACA  AAA  AUG  GAG  AAG  AUC  UUA  CCG  UCG  AUG  UUU  ACC       156
Phe  Ile  Asp  Leu  Thr  Lys  Met  Glu  Lys  Ile  Leu  Pro  Ser  Met  Phe  Thr
      15                   20                       25

CCU  GUA  AAG  AGU  GUU  AUG  UGU  UCC  AAA  GUU  GAU  AAA  AUA  AUG  GUU  CAU       204
Pro  Val  Lys  Ser  Val  Met  Cys  Ser  Lys  Val  Asp  Lys  Ile  Met  Val  His
 30                        35                       40                        45

GAG  AAU  GAG  UCA  UUG  UCA  GAG  GUG  AAC  CUU  UUU  AAA  GGA  GUU  AAG  CUU       252
Glu  Asn  Glu  Ser  Leu  Ser  Glu  Val  Asn  Leu  Phe  Lys  Gly  Val  Lys  Leu
                     50                        55                        60

AUU  GAU  AGU  GGA  UAC  GUC  UGU  UUA  GCC  GGU  UUG  GUC  GUC  ACG  GGC  GAG       300
Ile  Asp  Ser  Gly  Tyr  Val  Cys  Leu  Ala  Gly  Leu  Val  Val  Thr  Gly  Glu
               65                        70                        75

UGG  AAC  UUG  CCU  GAC  AAU  UGC  AGA  GGA  GGU  GUG  AGC  GUG  UGU  CUG  GUG       348
Trp  Asn  Leu  Pro  Asp  Asn  Cys  Arg  Gly  Gly  Val  Ser  Val  Cys  Leu  Val
          80                        85                        90

GAC  AAA  AGG  AUG  GAA  AGA  GCC  GAC  GAG  GCC  ACU  CUC  GGA  UCU  UAC  UAC       396
Asp  Lys  Arg  Met  Glu  Arg  Ala  Asp  Glu  Ala  Thr  Leu  Gly  Ser  Tyr  Tyr
     95                       100                       105

ACA  GCA  GCU  GCA  AAG  AAA  AGA  UUU  CAG  UUC  AAG  GUC  GUU  CCC  AAU  UAU       444
Thr  Ala  Ala  Ala  Lys  Lys  Arg  Phe  Gln  Phe  Lys  Val  Val  Pro  Asn  Tyr
110                       115                       120                       125

GCU  AUA  ACC  ACC  CAG  GAC  GCG  AUG  AAA  AAC  GUC  UGG  CAA  GUU  UUA  GUU       492
Ala  Ile  Thr  Thr  Gln  Asp  Ala  Met  Lys  Asn  Val  Trp  Gln  Val  Leu  Val
                130                       135                       140

AAU  AUU  AGA  AAU  GUG  AAG  AUG  UCA  GCG  GGU  UUC  UGU  CCG  CUU  UCU  CUG       540
Asn  Ile  Arg  Asn  Val  Lys  Met  Ser  Ala  Gly  Phe  Cys  Pro  Leu  Ser  Leu
          145                       150                       155
```

| | | | | | | | | | | | | | | | | |
|---|---|---|---|---|---|---|---|---|---|---|---|---|---|---|---|---|
| GAG | UUU | GUG | UCG | GUG | UGU | AUU | GUU | UAU | AGA | AAU | AAU | AUA | AAA | UUA | GGU | 588 |
| Glu | Phe | Val | Ser | Val | Cys | Ile | Val | Tyr | Arg | Asn | Asn | Ile | Lys | Leu | Gly | |
| | 160 | | | | 165 | | | | | 170 | | | | | | |
| UUG | AGA | GAG | AAG | AUU | ACA | AAC | GUG | AGA | GAC | GGA | GGG | CCC | AUG | GAA | CUU | 636 |
| Leu | Arg | Glu | Lys | Ile | Thr | Asn | Val | Arg | Asp | Gly | Gly | Pro | Met | Glu | Leu | |
| 175 | | | | 180 | | | | | 185 | | | | | | | |
| ACA | GAA | GAA | GUC | GUU | GAU | GAG | UUC | AUG | GAA | GAU | GUC | CCU | AUG | UCG | AUC | 684 |
| Thr | Glu | Glu | Val | Val | Asp | Glu | Phe | Met | Glu | Asp | Val | Pro | Met | Ser | Ile | |
| 190 | | | | | 195 | | | | | 200 | | | | | 205 | |
| AGG | CUU | GCA | AAG | UUU | CGA | UCU | CGA | ACC | GGA | AAA | AAG | AGU | GAU | GUC | CGC | 732 |
| Arg | Leu | Ala | Lys | Phe | Arg | Ser | Arg | Thr | Gly | Lys | Lys | Ser | Asp | Val | Arg | |
| | | | | 210 | | | | | 215 | | | | | 220 | | |
| AAA | GGG | AAA | AAU | AGU | AGU | AAU | GAU | CGG | UCA | GUG | CCG | AAC | AAG | AAC | UAU | 780 |
| Lys | Gly | Lys | Asn | Ser | Ser | Asn | Asp | Arg | Ser | Val | Pro | Asn | Lys | Asn | Tyr | |
| | | | | 225 | | | | | 230 | | | | | 235 | | |
| AGA | AAU | GUU | AAG | GAU | UUU | GGA | GGA | AUG | AGU | UUU | AAA | AAG | AAU | AAU | UUA | 828 |
| Arg | Asn | Val | Lys | Asp | Phe | Gly | Gly | Met | Ser | Phe | Lys | Lys | Asn | Asn | Leu | |
| | | 240 | | | | | 245 | | | | | 250 | | | | |
| AUC | GAU | GAU | GAU | UCG | GAG | GCU | ACU | GUC | GCC | GAA | UCG | GAU | UCG | UUU | UAA | 876 |
| Ile | Asp | Asp | Asp | Ser | Glu | Ala | Thr | Val | Ala | Glu | Ser | Asp | Ser | Phe | * | |
| | 255 | | | | | 260 | | | | | 265 | | | | | |
| AUA | CGC | UCG | ACG | AGA | UUU | UCA | GGA | GCU | AAG | GAA | GCU | AAA | AUG | GAG | AAA | 924 |
| Ile | Arg | Ser | Thr | Arg | Phe | Ser | Gly | Ala | Lys | Glu | Ala | Lys | Met | Glu | Lys | |
| 270 | | | | | 275 | | | | | 280 | | | | | 285 | |
| AAA | AUC | ACU | GGA | UAU | ACC | ACC | GUU | GAU | AUA | UCC | CAA | UCG | CAU | CGU | AAA | 972 |
| Lys | Ile | Thr | Gly | Tyr | Thr | Thr | Val | Asp | Ile | Ser | Gln | Ser | His | Arg | Lys | |
| | | | | 290 | | | | | 295 | | | | | 300 | | |
| GAA | CAU | UUU | GAG | GCA | UUU | CAG | UCA | GUU | GCU | CAA | UGU | ACC | UAU | AAC | CAG | 1020 |
| Glu | His | Phe | Glu | Ala | Phe | Gln | Ser | Val | Ala | Gln | Cys | Thr | Tyr | Asn | Gln | |
| | | | 305 | | | | | 310 | | | | | 315 | | | |
| ACC | GUU | CAG | CUG | GAU | AUU | ACG | GCC | UUU | UUA | AAG | ACC | GUA | AAG | AAA | AAU | 1068 |
| Thr | Val | Gln | Leu | Asp | Ile | Thr | Ala | Phe | Leu | Lys | Thr | Val | Lys | Lys | Asn | |
| | | 320 | | | | | 325 | | | | | 330 | | | | |
| AAG | CAC | AAG | UUU | UAU | CCG | GCC | UUU | AUU | CAC | AUU | CUU | GCC | CGC | CUG | AUG | 1116 |
| Lys | His | Lys | Phe | Tyr | Pro | Ala | Phe | Ile | His | Ile | Leu | Ala | Arg | Leu | Met | |
| | 335 | | | | | 340 | | | | | 345 | | | | | |
| AAU | GCU | CAU | CCG | GAA | UUC | CGU | AUG | GCA | AUG | AAA | GUU | UUC | CAU | GAG | CAA | 1164 |
| Asn | Ala | His | Pro | Glu | Phe | Arg | Met | Ala | Met | Lys | Val | Phe | His | Glu | Gln | |
| 350 | | | | | 355 | | | | | 360 | | | | | 365 | |
| ACU | GAA | ACG | UUU | UCA | UCG | CUC | UGG | AGU | GAA | UAC | CAC | GAC | GAU | UUC | CGG | 1212 |
| Thr | Glu | Thr | Phe | Ser | Ser | Leu | Trp | Ser | Glu | Tyr | His | Asp | Asp | Phe | Arg | |
| | | | | 370 | | | | | 375 | | | | | 380 | | |
| CAG | UUU | CUA | CAC | AUA | UAU | UCG | CAA | GAU | GUG | GCG | UGU | UAC | GGU | GAA | AAC | 1260 |
| Gln | Phe | Leu | His | Ile | Tyr | Ser | Gln | Asp | Val | Ala | Cys | Tyr | Gly | Glu | Asn | |
| | | | 385 | | | | | 390 | | | | | 395 | | | |
| CUG | GCC | UAU | UUC | CCU | AAA | GGG | UUU | AUU | GAG | AAU | AUG | UUU | UUC | GUC | UCA | 1308 |
| Leu | Ala | Tyr | Phe | Pro | Lys | Gly | Phe | Ile | Glu | Asn | Met | Phe | Phe | Val | Ser | |
| | | 400 | | | | | 405 | | | | | 410 | | | | |
| GCC | AAU | CCC | UGG | GUG | AGU | UUC | ACC | AGU | UUU | GAU | UUA | AAC | GUG | GCC | AAU | 1356 |
| Ala | Asn | Pro | Trp | Val | Ser | Phe | Thr | Ser | Phe | Asp | Leu | Asn | Val | Ala | Asn | |
| | 415 | | | | | 420 | | | | | 425 | | | | | |
| AUG | GAC | AAC | UUC | UUC | GCC | CCC | GUU | UUC | ACC | AUG | GGC | AAA | UAU | UAU | ACG | 1404 |
| Met | Asp | Asn | Phe | Phe | Ala | Pro | Val | Phe | Thr | Met | Gly | Lys | Tyr | Tyr | Thr | |
| 430 | | | | | 435 | | | | | 440 | | | | | 445 | |
| CAA | GGC | GAC | AAG | GUG | CUG | AUG | CCG | CUG | GCG | AUU | CAG | GUU | CAU | CAU | GCC | 1452 |
| Gln | Gly | Asp | Lys | Val | Leu | Met | Pro | Leu | Ala | Ile | Gln | Val | His | His | Ala | |
| | | | | 450 | | | | | 455 | | | | | 460 | | |
| GUC | UGU | GAU | GGC | UUC | CAU | GUC | GGC | AGA | AUG | CUU | AAU | GAA | UUA | CAA | CAG | 1500 |
| Val | Cys | Asp | Gly | Phe | His | Val | Gly | Arg | Met | Leu | Asn | Glu | Leu | Gln | Gln | |
| | | | 465 | | | | | 470 | | | | | 475 | | | |

```
UAC  UGC  GAU  GAG  UGG  CAG  GGC  GGG  GCG  UAAUUUUUUU  AAGGCAGUUA              1547
Tyr  Cys  Asp  Glu  Trp  Gln  Gly  Gly  Ala
               480                 485

UUGGUGCCCU  UAAACGCCUG  GUGCUACGCC  UGAAUAAGUG  AUAAUAAGCG  GAUGAAUGGC            1607

AGAAAUUCGU  CGAGGGUAGU  CAAGAUGCAU  AAUAAAUAAC  GGAUUGUGUC  CGUAAUCACA            1667

CGUGGUGCGU  ACGAUAACGC  AUAGUGUUUU  UCCCUCCACU  UAAAUCGAAG  GGUUGUGUCU            1727

UGGAUCGCGC  GGGUCAAAUG  UAUAUGGUUC  AUAUACAUCC  GCAGGCACGU  AAUAAAGCGA            1787

GGGGUUCGAA  UCCCCCCGUU  ACCCCCGGUA  GGGGCCCA                                      1825
```

( 2 ) INFORMATION FOR SEQ ID NO:2:

( i ) SEQUENCE CHARACTERISTICS:
        ( A ) LENGTH: 268 amino acids
        ( B ) TYPE: amino acid
        ( D ) TOPOLOGY: linear ( i i ) MOLECULE TYPE: protein ( x i ) SEQUENCE DESCRIPTION: SEQ ID NO:2:

```
Met  Ala  Leu  Val  Val  Lys  Gly  Lys  Val  Asn  Ile  Asn  Glu  Phe  Ile  Asp
 1              5                    10                            15

Leu  Thr  Lys  Met  Glu  Lys  Ile  Leu  Pro  Ser  Met  Phe  Thr  Pro  Val  Lys
              20                  25                           30

Ser  Val  Met  Cys  Ser  Lys  Val  Asp  Lys  Ile  Met  Val  His  Glu  Asn  Glu
              35                  40                           45

Ser  Leu  Ser  Glu  Val  Asn  Leu  Phe  Lys  Gly  Val  Lys  Leu  Ile  Asp  Ser
         50                   55                          60

Gly  Tyr  Val  Cys  Leu  Ala  Gly  Leu  Val  Val  Thr  Gly  Glu  Trp  Asn  Leu
 65                    70                          75                       80

Pro  Asp  Asn  Cys  Arg  Gly  Gly  Val  Ser  Val  Cys  Leu  Val  Asp  Lys  Arg
                    85                  90                           95

Met  Glu  Arg  Ala  Asp  Glu  Ala  Thr  Leu  Gly  Ser  Tyr  Tyr  Thr  Ala  Ala
                   100                 105                          110

Ala  Lys  Lys  Arg  Phe  Gln  Phe  Lys  Val  Val  Pro  Asn  Tyr  Ala  Ile  Thr
          115                     120                          125

Thr  Gln  Asp  Ala  Met  Lys  Asn  Val  Trp  Gln  Val  Leu  Val  Asn  Ile  Arg
          130                     135                     140

Asn  Val  Lys  Met  Ser  Ala  Gly  Phe  Cys  Pro  Leu  Ser  Leu  Glu  Phe  Val
145                     150                      155                       160

Ser  Val  Cys  Ile  Val  Tyr  Arg  Asn  Asn  Ile  Lys  Leu  Gly  Leu  Arg  Glu
                    165                      170                     175

Lys  Ile  Thr  Asn  Val  Arg  Asp  Gly  Gly  Pro  Met  Glu  Leu  Thr  Glu  Glu
                    180                      185                     190

Val  Val  Asp  Glu  Phe  Met  Glu  Asp  Val  Pro  Met  Ser  Ile  Arg  Leu  Ala
               195                      200                     205

Lys  Phe  Arg  Ser  Arg  Thr  Gly  Lys  Lys  Ser  Asp  Val  Arg  Lys  Gly  Lys
     210                     215                      220

Asn  Ser  Ser  Asn  Asp  Arg  Ser  Val  Pro  Asn  Lys  Asn  Tyr  Arg  Asn  Val
225                     230                      235                       240

Lys  Asp  Phe  Gly  Gly  Met  Ser  Phe  Lys  Lys  Asn  Asn  Leu  Ile  Asp  Asp
               245                      250                     255

Asp  Ser  Glu  Ala  Thr  Val  Ala  Glu  Ser  Asp  Ser  Phe
               260                      265
```

( 2 ) INFORMATION FOR SEQ ID NO:3:

-continued (i) SEQUENCE CHARACTERISTICS:
　　(A) LENGTH: 217 amino acids
　　(B) TYPE: amino acid
　　(D) TOPOLOGY: linear (ii) MOLECULE TYPE: protein (xi) SEQUENCE DESCRIPTION: SEQ ID NO:3:

```
Ile Arg Ser Thr Arg Phe Ser Gly Ala Lys Glu Ala Lys Met Glu Lys
 1               5                  10                  15

Lys Ile Thr Gly Tyr Thr Thr Val Asp Ile Ser Gln Ser His Arg Lys
            20                  25                  30

Glu His Phe Glu Ala Phe Gln Ser Val Ala Gln Cys Thr Tyr Asn Gln
        35                  40                  45

Thr Val Gln Leu Asp Ile Thr Ala Phe Leu Lys Thr Val Lys Lys Asn
     50                  55                  60

Lys His Lys Phe Tyr Pro Ala Phe Ile His Ile Leu Ala Arg Leu Met
 65                  70                  75                  80

Asn Ala His Pro Glu Phe Arg Met Ala Met Lys Val Phe His Glu Gln
                 85                  90                  95

Thr Glu Thr Phe Ser Ser Leu Trp Ser Glu Tyr His Asp Asp Phe Arg
            100                 105                 110

Gln Phe Leu His Ile Tyr Ser Gln Asp Val Ala Cys Tyr Gly Glu Asn
         115                 120                 125

Leu Ala Tyr Phe Pro Lys Gly Phe Ile Glu Asn Met Phe Phe Val Ser
     130                 135                 140

Ala Asn Pro Trp Val Ser Phe Thr Ser Phe Asp Leu Asn Val Ala Asn
145                 150                 155                 160

Met Asp Asn Phe Phe Ala Pro Val Phe Thr Met Gly Lys Tyr Tyr Thr
                 165                 170                 175

Gln Gly Asp Lys Val Leu Met Pro Leu Ala Ile Gln Val His His Ala
             180                 185                 190

Val Cys Asp Gly Phe His Val Gly Arg Met Leu Asn Glu Leu Gln Gln
         195                 200                 205

Tyr Cys Asp Glu Trp Gln Gly Gly Ala
     210                 215
```